United States Patent [19]

Pickens et al.

[11] Patent Number: 4,987,225

[45] Date of Patent: Jan. 22, 1991

[54] REMOVAL OF WATER MISCIBLE MATERIALS FROM GLYCOSIDE MIXTURES

[75] Inventors: Carl Pickens; Patrick M. McCurry, both of Decatur, Ill.

[73] Assignee: Henkel Kommanditgesellschaft auf Aktien, Duesseldorf, Fed. Rep. of Germany

[21] Appl. No.: 290,535

[22] Filed: Dec. 23, 1988

[51] Int. Cl.$^5$ .................. C07H 15/00; C07H 1/00; C08B 37/00; A61K 31/00

[52] U.S. Cl. .................... 536/124; 536/18.6; 536/127

[58] Field of Search ............. 536/18.6, 124, 127; 514/25, 54

[56] References Cited

U.S. PATENT DOCUMENTS

| | | | |
|---|---|---|---|
| 2,001,925 | 5/1935 | Thurber | 127/66 |
| 3,219,656 | 11/1965 | Boettner | 536/18.3 |
| 3,450,690 | 6/1969 | Gibbons et al. | 536/18.5 |
| 3,547,828 | 12/1970 | Mansfield et al. | 252/351 |
| 3,598,865 | 8/1971 | Lew | 536/4.1 |
| 3,707,535 | 12/1972 | Lew | 536/18.6 |
| 3,772,269 | 11/1973 | Lew | 536/4.1 |
| 3,839,318 | 10/1974 | Mansfield | 536/18.6 |
| 4,349,669 | 9/1982 | Klahr | 536/127 |
| 4,393,203 | 7/1983 | Mao et al. | 536/124 |
| 4,472,170 | 9/1984 | Hellyer | 44/51 |
| 4,483,979 | 11/1984 | Mao | 536/18.6 |
| 4,510,306 | 4/1985 | Langdon | 536/127 |
| 4,597,770 | 7/1986 | Forand et al. | 44/51 |
| 4,704,453 | 11/1987 | Lorenz et al. | 536/18.6 |
| 4,713,447 | 12/1987 | Letton | 536/18.6 |

FOREIGN PATENT DOCUMENTS

| | | |
|---|---|---|
| 92355 | 4/1983 | European Pat. Off. . |
| 96917 | 5/1983 | European Pat. Off. . |
| 132043 | 6/1984 | European Pat. Off. . |
| 328959 | 2/1989 | European Pat. Off. . |

*Primary Examiner*—Ronald W. Griffin
*Assistant Examiner*—Everett White
*Attorney, Agent, or Firm*—Ernest G. Szoke; Wayne C. Jaeschke; Daniel S. Ortiz

[57] ABSTRACT

Undesired hydrophilic materials are readily removed from long chain hydrophobic alcohols, from long chain hydrophobic alcohol/glycoside surfactant mixtures and from solutions of glycoside surfactants in water immiscible solvents resulting from dissolving the glycoside surfactants in said solvents or mixing aqueous mixtures of glycoside surfactants with said solvents, by contacting the hydrophilic material containing hydrophobic composition with water in an amount, and for a time period sufficient, to extract at least a portion of the hydrophilic material from the hydrophobic composition and to form a separate aqueous phase and by separating the resulting aqueous phase from the hydrophobic composition. The process is particularly useful when employed in the context of a glycoside surfactant manufacturing process to remove polysaccharide by-products from a crude unreacted hydrophobic alcohol/glycoside surfactant reaction product mixture at a stage prior to the separation of the hydrophobic alcohol from the glycoside surfactant.

30 Claims, No Drawings ns and, in particular to the removal of polysaccharide constituents and other materials from glycoside surfactant/hydrophobic alcohol or other hydrophobic solvent compositions or from polysaccharide-containing mixed hydrophobic alcohol/glycoside surfactant compositions. In one embodiment, the invention involves a glycoside surfactant manufacturing process wherein the indicated polysaccharide removal technique is applied to a crude polysaccharide-containing hydrophobic alcohol/glycoside surfactant reaction product mixture prior to the evaporative separation of the hydrophobic alcohol from the desired glycoside surfactant product.

REMOVAL OF WATER MISCIBLE MATERIALS FROM GLYCOSIDE MIXTURES

BACKGROUND OF THE INVENTION

1. Field of the Invention:

This invention pertains generally to a process for removing undesired polysaccharide and other hydrophilic constituents from hydrophobic compositions containing same and, in particular to the removal of polysaccharide constituents and other materials from glycoside surfactant/hydrophobic alcohol or other hydrophobic solvent compositions or from polysaccharide-containing mixed hydrophobic alcohol/glycoside surfactant compositions. In one embodiment, the invention involves a glycoside surfactant manufacturing process wherein the indicated polysaccharide removal technique is applied to a crude polysaccharide-containing hydrophobic alcohol/glycoside surfactant reaction product mixture prior to the evaporative separation of the hydrophobic alcohol from the desired glycoside surfactant product.

In accordance with the process there is provided certain novel glycoside surfactant compositions which have an average of at least 9 carbon atoms in the hydrophobic aglycone substituent thereof and an average degree of polymerization (D.P.) of at least 1.2 and which are essentially free of (i.e., contain, on a total glycoside surfactant weight basis, less than 0.5 weight percent of) undesired polysaccharide constituents and which contain, on a total glycoside surfactant weight basis, less than 5 (preferably less than 1) weight percent of polyglycoside species or constituents having a degree of polymerization of 10 or above. The process is useful for purifying alkyl polyglycoside products to produce a refined material for special uses. 2. Statement of Related Art:

Long chain alkyl monoglycosides and long chain alkyl polyglycosides and mixtures thereof (hereinafter generically referred to as "glycoside surfactants") are known materials, are known to be surface active in character and are known to be useful in a wide variety of household and industrial applications. Moreover, it is also known that glycoside surfactants can be prepared by reacting a long chain alcohol with a saccharide reactant (e.g., a monosaccharide or a material hydrolyzable to a monosaccharide) at an elevated temperature in the presence of an acid catalyst.

Processes for preparing alkyl glycoside compositions are disclosed in U.S. Pat. No. 3,219,656 to Boettner (issued Nov. 23, 1965); U.S. Pat. No. 3,547,828 to Mansfield et al. (issued Dec. 15, 1970); U.S. Pat. No. 3,598,865 to Lew (issued Aug. 10, 1971); U.S. Pat. No. 3,707,535 to Lew (issued Dec. 26, 1972); U.S. Pat. No. 3,772,269 to Lew (issued Nov. 13, 1973); U.S. Pat. No. 3,839,318 to Mansfield (issued Oct. 1, 1974); U.S. Pat. No. 4,349,669 to Klahr (issued Sept. 14, 1982); U.S. Pat. No. 4,393,203 to Mao et al. (issued Jul. 12, 1983); U.S. Pat. No. 4,472,170 to Hellyer (issued Sept. 18, 1984); U.S. Pat. No. 4,510,306 to Langdon (issued Apr. 9, 1985); U.S. Pat. No. 4,597,770 to Forand et al. (issued Jul. 1, 1986); U.S. Pat. No. 4,704,453 to Lorenz et al. (issued Nov. 3, 1987): U.S. Pat. No. 4,713,447 to Letton (issued Dec. 15, 1987); published European Application No. 83302002.7 (EPO Publication No. 0092355; Vander Burgh et al; published Oct. 26, 1983); published European Application No. 83200771.0 (EPO Publication No.0096917; Farris; published Dec. 28, 1983); and published European Application No. 84303874.6 (EPO Publication 0132043; published Jan. 23, 1985).

During the course of the aforementioned acid-catalyzed saccharide reactant/long chain alcohol reaction process, there is usually employed a substantial stoichiometric excess of the long chain alcohol reactant. The resulting reaction product mixture as initially made (i.e., without any intervening separation, fractionation or purification operations) typically contains a substantial quantity of residual unreacted long chain alcohol, the monoglycoside of the long chain alcohol as the predominant glycoside molecular species on a mole percentage basis, the various higher degree of polymerization long chain alcohol polyglycoside species in progressively decreasing mole percentage amounts or proportions, substantial but variable amounts of polysaccharide byproducts which do not have long chain alcohol molecules chemically attached (or covalently bonded) thereto and miscellaneous materials such as catalysts, processing aids and the like.

In accordance with the various prior art references, it has been conventional practice to remove the residual unreacted long chain alcohol from the indicated reaction mixture via various techniques such as vacuum distillation, organic solvent (e.g., acetone) extraction or fractionation, and thin (or wiped) film evaporation.

If the long chain (fatty) alcohol is removed from the reaction mixture by one of the distillation or evaporation methods, the polysaccharide by products and any other materials with low volatility remain in the alkyl glycoside product.

The presence of the aforementioned polysaccharide byproducts and other impurities in the long chain (or "fatty") alcohol-containing reaction mixture can result in the development of unacceptable properties (e.g. high viscosities) and/or in the development of dark-colored insoluble particulate matter and/or in fouling of heat transfer surfaces during evaporative removal of the unreacted fatty alcohol from the reaction mixture using wiped or thin film evaporation equipment.

In addition, certain applications require an alkyl glycoside surfactant product with a low content of non-alkyl glycoside materials. The method of the present invention can be used to reduce the concentration of certain non-alkyl glycoside hydrophilic or water miscible components in an alkyl glycoside surfactant product.

SUMMARY OF THE INVENTION

It has also been discovered that the foregoing problems can be essentially eliminated by way of a process wherein the indicated polysaccharide by-products and other hydrophilic materials are extracted from alkyl glycoside surfactant, or the above-discussed long chain alcohol-containing hydrophobic reaction mixture by intimately contacting the product in solution in a water immiscible solvent or the reaction mixture with water and thereafter separating the resulting aqueous phase from the water immiscible solvent phase.

Accordingly, the present invention, in one aspect, is an aqueous contacting process for removing undesired polysaccharide materials from hydrophobic compositions which contain the polysaccharide materials in admixture with a long chain hydrophobic alcohol and/or a glycoside surfactant material. The process comprises intimately admixing the hydrophobic composition with water in an amount sufficient to form a separate aqueous phase and for a time period sufficient to extract at least a portion of the polysaccharide material from the hydrophobic composition (to form a separate polysaccharide-rich aqueous phase) and thereafter separating the resulting polysaccharide-rich aqueous composition from the hydrophobic composition. The process preferably removes a substantial portion of the polysaccharide by product from the water immiscible solvent phase.

In another aspect of the invention, a long chain alkyl glycoside or polyglycoside or a glycoside surfactant composition is dissolved in a water immiscible solvent and contacted with water to extract any water miscible materials in the alkyl glycoside or alkyl polyglycoside product. The water is present in at least a sufficient amount to provide a separate aqueous phase. The water immiscible solvent can be the alcohol from which the aglycone portion of the glycoside surfactant is derived.

In another embodiment of the invention an aqueous solution of the glycoside surfactant is contacted with a solvent for the glycoside surfactant, which is immiscible with water, the glycoside surfactant partitioned into the water immiscible solvent. The hydrophilic impurities remain in the water phase.

In another of its aspects, the present invention is embodied in a process for the preparation of a glycoside surfactant, said process comprising the steps of:
(a) reacting a long chain hydrophobic alcohol with a saccharide reactant at an elevated temperature and in the presence of an acid catalyst to produce a hydrophobic reaction product mixture comprising unreacted long chain hydrophobic alcohol, glycoside surfactant and polysaccharide by-product;
(b) treating said reaction product mixture by contacting the neutralized reaction product mixture with water in an amount ranging from about 1 to about 50 parts by weight of water per 100 parts by weight of the reaction product mixture for a time period sufficient to extract at least a substantial portion of the polysaccharide by-product out of the reaction product mixture and into the water and thereafter forming a separate polysaccharide containing aqueous phase and a purified hydrophobic reaction product phase;
(c) separating the polysaccharide-containing aqueous phase from the purified hydrophobic reaction product phase; and
(d) thereafter removing substantially all of the unreacted hydrophobic alcohol from the purified hydrophobic reaction product phase.

The processes of the present invention provide a means for obtaining long chain hydrophobic alcohol-based compositions which are substantially free of (or which at least contain substantially reduced levels of) hydrophilic polysaccharide materials and other hydrophilic impurities. Moreover, the processes also provide a means for obtaining glycoside surfactant/long chain hydrophobic alcohol solutions which are capable of being satisfactorily processed through a wiped film evaporator to thereby separate the hydrophobic alcohol from the glycoside surfactant to produce a melt having relatively lower viscosity than it would otherwise have while avoiding the presence and/or formation of insoluble particulate matter and thereby avoiding fouling (or carbonizing) of the heat transfer surfaces of the evaporator during the course of the evaporation process.

The aforementioned processes are particularly well suited for use, and especially efficient when used, in connection with hydrophobic alcohols containing an average of 9 or more (especially 10 or 11 or more) carbon atoms and/or with glycoside surfactants having an average of 9 or more (especially 10 or 11 or more) carbon atoms in the aglycone portion thereof. When so used, the processes provide certain novel glycoside surfactant compositions which have an average of at least 9 (preferably an average of at least 10 or 11) carbon atoms in the hydrophobic aglycone substituent thereof and average degree of polymerization of at least 1.2 and which contain, on a total glycoside surfactant weight basis, less than 0.5 (preferably less than 0.25, more preferably less than 0.1 and most preferably less than 0.01) weight percent hydrophilic polysaccharide constituents and less than 5 (preferably less than 1) weight percent of polyglycoside species having a degree of polymerization of 10 or more.

DETAILED DESCRIPTION OF THE INVENTION

Glycoside surfactants which can be suitably prepared and/or long chain hydrophobic alcohol solutions of which can be suitably treated or purified in accordance with the present invention include those of the formula:

$$RO(R^1O)_y(Z)_x \qquad (A)$$

wherein the hydrophobic aglycone substituent, R, is a monovalent organic radical (e.g., a monovalent saturated aliphatic, unsaturated aliphatic or aromatic radical such as alkyl, hydroxyalkyl, alkenyl, hydroxyalkenyl, aryl, alkylaryl, hydroxyalkylaryl, arylalkyl, alkenylaryl, arylalkenyl, etc.) containing from about 8 to about 30 (preferably from about 10 to about 24 and more preferably from 10 to about 18) carbon atoms; O is an oxygen atom; $R^1$ is a divalent hydrocarbon radical containing from 2 to about 4 carbon atoms (preferably the —$R^1$O—group is ethylene oxide, propylene oxide, or random or block combinations thereof); y is a number having an average value of from 0 to about 12 (preferably y is zero); Z is a moiety (i.e., a glycosyl group) derived from a reducing saccharide containing 5 or 6 carbon atoms (e.g., glucose, fructose, mannose, galactose, talose, gulose, allose, altrose, idose, arabinose, xylose, lyxose and ribose); and x represents the average degree of polymerization, D.P., and is a number having an average value of from 1 to about 5 (preferably from 1 to about 3).

Glycoside surfactants which are particularly preferred include those wherein the glycosyl group, Z, is derived from arabinose, xylose, glucose, mannose, galactose or mixtures thereof (especially glucose); wherein the aglycone group, R, is a monovalent aliphatic group which contains from about 10 to about 18 (especially from about 12 to about 18) carbon atoms; and wherein the average value of x is from approximately 1.1 to about 2.5 (especially from about 1.2 to about 1.8).

The treatment or purification method hereof is especially efficient and effective when used in connection with (i.e., when practiced upon) relatively more hydrophobic glycoside surfactant materials (e.g., those wherein the hydrophobic aglycone group, R, contains at least about 11 or 12 carbon atoms and wherein the average degree of polymerization, x, is about 1.5 or less) and when the glycoside surfactant material to be so-treated is in the form of moderately low glycoside surfactant solids-containing hydrophobic alcohol solution (e.g., wherein the glycoside surfactant material constitutes from about 5 to about 40, preferably from about 5 to about 35 and more preferably from about 5 to about 30, weight percent of said hydrophobic alcohol solution). While the indicated treatment or purification method can, in fact, be suitably employed in connection with relatively less hydrophobic glycoside surfactant and/or in connection with more concentrated (i.e.,-higher glycoside surfactant solids-containing) glycoside surfactant/hydrophobic alcohol solutions, such is generally somewhat less desirable in that it is generally accompanied or characterized by somewhat increased glycoside surfactant losses to (i.e., partitioning or dissolution within) the resulting separate aqueous phase.

Novel glycoside surfactant compositions which can be prepared in accordance herewith include those wherein the hydrophobic aglycone substituent, R, contains an average of at least 9 (preferably at least 10 or 11) carbon atoms and wherein the average degree of polymerization (i.e., the average "x" value thereof) is at least 1.2 and which contain, on a total glycoside surfactant weight basis, less than 0.5 (preferably less than 0.25, more preferably less than 0.1 and most preferably less than 0.01) weight percent of hydrophilic polysaccharide constituents and less than 5 (preferably less than 2 and more preferably less than 1) weight percent of polyglycoside species which generally correspond to the formula A above except for having a degree of polymerization (i.e., individual molecule "x" values) of 10 or more. As a general rule, the glycoside surfactant constituents of the formula A above constitute the predominant portion (i.e., more than 50%) by weight of the indicated compositions and oftentimes said formula (A) constituents at least about 90 (more preferably at least about 93 and most preferably at least about 95) percent of the total weight of said compositions.

In the further aspect of the invention, a long chain alkyl glycoside surfactant product, as defined above (alkyl group contains at least 8 carbon atoms) containing hydrophilic impurities therein can be dissolved in or extracted into, a water immiscible solvent or hydrophobic solvent for the alkyl glycoside surfactant in the presence of a sufficient amount of water to form a separate phase, the water phase separated from the water immiscible solvent phase and the alkyl glycoside surfactant recovered from the water immiscible or hydrophobic solvent.

The water immiscible solvent can be the same hydrophobic alcohol from which the aglycone group was formed or can be a different hydrophobic alcohol or a solvent such as toluene, xylene, di-n-butyl ether, perchloroethylene and the like. It is preferred that the water immiscible solvent have a low boiling point so that it can be easily separated from the alkyl glycoside composition after the mixture has been contacted with the water.

The separated water phase, contains the water soluble or hydrophilic impurities (e.g. catalyst salts) and some dissolved alkyl glycoside material. The alkyl glycoside material is predominantly the alkyl glycoside material with the higher degree of polymerization (D.P.) or value of x in the formula supra.

Long chain hydrophobic alcohols from which the indicated glycoside surfactants can be prepared are preferably monohydric aliphatic alcohols containing from about 8 to about 30 (preferably from about 10 to about 24, more preferably from about 10 to about 18 and most preferably from about 12 to about 18) carbon atoms.

Saccharide reactants which can be employed to prepare the aforementioned glycoside surfactants include reducing monosaccharide materials containing 5 or 6 carbon atoms such as, for example, glucose, galactose, mannose, xylose, arabinose, fructose, etc. as well as materials which are hydrolyzable to form monosaccharides such as lower alkyl glycosides (e.g., methyl glycoside, ethyl glycoside, propyl glycoside, butyl glycoside, etc.), oligosaccharides (e.g., sucrose, maltose, maltotriose, lactose, xylobiose, melibiose, cellobiose, raffinose, stachyose, etc.) and polysaccharides such as starch. Such saccharide reactants may be employed in dry (e.g., anhydrous) form or, if desired, may be employed in the form of aqueous solutions thereof.

The reaction between the hydrophobic alcohol reactant and the saccharide reactant to form the glycoside surfactant is typically conducted at an elevated temperature and in the presence of an acid catalyst. As a general rule, said reaction is preferably conducted at a temperature of from about 80° to about 140° C. and is more preferably conducted at a temperature in the range of from abut 90° to about 120° C.

Acid catalysts suitable for use herein include strong mineral acids such as hydrochloric acid, sulfuric acid, nitric acid, phosphoric acid, hypophosphorous acid, etc.; strong organic acids such as para toluenesulfonic acid, methanesulfonic acid, triflouromethanesulfonic acid, mono- or polyalkylated aryl mono- or polysulfonic acids such as dodecylbenzenesulfonic acid, etc.; and macroreticular acidic ion exchange resins such as macroreticular sulfonic acid ion exchange resins, perfluorinatedsulfonic acid resins, etc. Typically, said acid catalyst will be employed in an amount ranging from about 0.0005 to about 0.03 (preferably from about 0.002 to about 0.015) moles thereof per mole of saccharide used.

The reaction of the saccharide reactant and the alcohol reactant in accordance with the present invention is a condensation reaction in which a molecule of water is liberated or generated for each instance in which a molecule of alcohol reacts with a monosaccharide molecule. Since such reaction is reversible in character, it is typically desirable to remove water from the reaction mixture during the course of the reaction in order to shift the equilibrium in favor of the desired glycoside product. The reaction is generally conducted at a pressure which facilitates water removal while at the same time maintaining the desired reaction temperature. As a general rule, the reaction is advantageously conducted at a pressure in the range of from about 1 to about 100 (preferably from about 10 to about 60) mm Hg (absolute).

Typically, the above-described reaction process will be conducted over a reaction period of from about 1 to about 20 (preferably from about 2 to about 10) hours.

The amount of undesired polysaccharide by-product generated during the course of the reaction process can vary considerably depending upon a variety of factors such as, for example, the exact nature or identity and purity of the alcohol and saccharide reactants employed, the catalyst selected for use and the reaction conditions employed, the degree of care exercised in running and controlling the reaction while it is in progress, the average degree of polymerization (D.P) (i.e., the average "x" value) of the glycoside surfactant product to be produced thereby, and the like. However, it can as a general rule or observation be noted that the amount of undesired polysaccharide by-product generated will progressively increase with increases in the average D.P. (i.e., the average "x" value) of the glycoside surfactant product to be produced. Even in the case of well-run, carefully controlled reactions using relatively pure reactants and carefully selected catalyst materials to produce glycoside surfactant having only a moderate D.P. the amount of polysaccharide by-product generated can generally be expected to vary as a function of D.P. as follows;

| Average D.P. | Amount of Polysaccharide By-Product Generated (weight percent, glycoside surfactant weight basis) |
|---|---|
| 1.1 | at least about 0.6% |
| 1.2 | at least about 1.2% |
| 1.3 | at least about 1.8% |
| 1.4 | at least about 2.4% |
| 1.5 | at least about 3.0% |
| 1.6 | at least about 3.6% |

Upon completion of the reaction, the acid catalyst can either be neutralized or removed from the reaction mixture (e.g., by way of centrifugation or filtration in the case of insoluble acidic ion exchange resins) or, in the event that the catalyst is a substantially water soluble material, it can be left in unneutralized form for subsequent removal (i.e., along with the undesired polysaccharide by-products) during the hereinafter discussed aqueous extraction process. In this latter case, the extraction/separation operation is preferably conducted under relatively low temperature and short time conditions in order to minimize hydrolytic reversing reactions.

As has been noted above, a key feature of the present invention resides in the removal of undesired polysaccharide materials from hydrophobic compositions (e.g., long chain hydrophobic alcohol compositions, mixed long chain hydrophobic alcohol/glycoside surfactant compositions such as the crude reaction product of the above-discussed saccharide reactant/hydrophobic alcohol reaction process, solutions of glycoside surfactant compositions, and the like) by way of an aqueous contacting procedure.

In accordance with the present process, the hydrophobic composition is contacted (preferably repetitively contacted) with water in an amount and for a time sufficient to extract at least a substantial portion of the undesired polysaccharide material from the hydrophobic composition to form a separate and distinct aqueous solution phase and the resulting aqueous solution phase thereafter separated from the hydrophobic composition.

Naturally, the amount of water employed in connection with the foregoing procedure is controlled or adjusted so as to be sufficient to remove the desired amount or proportion of water soluble material from the hydrophobic composition and must, in any event, be sufficient to exceed the aqueous saturation point of the hydrophobic composition and thus form the separate aqueous phase. Typically, the amount of water employed ranges from about 1 to about 50 (preferably from about 2 to about 40 and more preferably from about 2 to about 30) parts by weight of water per 100 parts of the hydrophobic composition.

In one preferred embodiment of the invention, the aqueous contacting procedure is performed as a multistep (especially a 2 or 3 step) process wherein from about 10 to about 40 (preferably from about 20 to about 30) parts by weight of water per 100 parts by weight of the polysaccharide-containing hydrophobic composition is employed in a first aqueous contacting step and wherein from about 5 to about 25 (preferably from about 10 to about 20) parts by weight of water per 100 parts by weight of the hydrophobic composition is employed in a second aqueous contacting step. Alternatively, a centrifugal countercurrent extraction/separation technique can be employed.

While the temperature and pressure conditions under which the indicated aqueous contacting operation is conducted are not particularly critical, the contacting is typically conducted at a temperature of from about 25° to about 120° (preferably from about 45° to about 90°) C. and at a pressure of about 600 to about 1000 (preferably from about 700 to about 900) mm Hg (absolute).

The time period over which the aqueous contacting/separation process is conducted is not particularly critical but typically is in the range of from about 1 to about 18 (preferably from about 2 to about 8) hours. In the case of the centrifugal countercurrent procedure, a matter of seconds has been found to be sufficient.

The step of separating the aqueous phase from the hydrophobic composition following the above-described contacting process can be conducted in any convenient, conventional fashion such as, for example, permitting the two phases to separate into an upper and lower layer and thereafter separating one layer from the other (e.g., by decanting, drawing off one layer, etc.) or via the use of a centrifuge, etc. In one especially preferred embodiment, however, the extraction and separation steps are conducted in a continuous (or semi-continuous) fashion utilizing a countercurrent centrifuge.

Polysaccharide-containing hydrophobic compositions which can be suitably treated in accordance with the foregoing process include any such composition which has a water soluble polysaccharide constituent dissolved or dispersed in a hydrophobic material such as, for example, long chain hydrophobic alcohols, relatively water insoluble glycoside surfactants, hydrophobic alcohol/glycoside surfactant solutions, water-immiscible solvent solutions and the like.

Hydrophobic compositions suitably treated in accordance with the invention specifically include compositions which comprise, on a total composition weight basis, (a) from about 95 to about 50 (preferably from about 90 to about 60) parts by weight of a long chain hydrophobic alcohol or water immiscible solvent; (b) from about 4 to about 45 (preferably from about 8 to about 35) parts by weight of a glycoside surfactant; and (c) from about 0.5 to about 10 (oftentimes from about 1.0 to about 8) parts by weight of the aforementioned polysaccharide material.

As has been noted above, the process of the invention is particularly effective in removing a substantial proportion of the polysaccharide material initially contained within the hydrophobic composition of interest. Thus for example, when the hydrophobic composition initially contains from about 1 to about 10 weight percent of the polysaccharide material on a total weight basis, the polysaccharide content can be readily reduced to a value of less than 1 (preferably less than 0.3 and more preferably less than 0.1) weight percent on a total weight basis following said extraction process.

During the course of the aforementioned process, the hydrophobic composition being treated, or the water immiscible solvent solution of the glycoside surfactant will naturally become saturated with some, typically minor, amount of water. While the exact, quantitative amount of water absorbed into the hydrophobic or water immiscible composition in a given instance will depend upon the nature, identity, degree of hydrophobicity, temperature and the like of the particular composition involved, the amount of absorbed water will typically be less than about 25 (more typically less than about 15) weight percent of the extracted hydrophobic composition. The water immiscible solvents and temperature of the process should be selected to minimize the amount of water absorbed.

While the small amount of water can, if desired, be left in the extracted hydrophobic composition, it can also (i.e., where removal of the water therefrom is desired) be readily and conveniently removed by evaporation in a thin film evaporator apparatus. Operating conditions for a thin film evaporation apparatus for water removal purposes will typically involve a temperature of from about 50° to about 250° (preferably from about 130° to about 220)° C. and a pressure of from about 100 to about 1000 (preferably from about 200 to about 760) mm Hg (absolute). Operation at the relatively higher temperatures is preferred in order to avoid foam formation during the water removal process.

In instances wherein the hydrophobic composition of concern is of a type which comprises a solution of a glycoside surfactant in a long chain hydrophobic alcohol (e.g., such as the reaction product resulting from the glycoside surfactant preparation process), it will oftentimes be desired to separate the long chain hydrophobic alcohol from the glycoside surfactant. The separation can be conveniently accomplished using a thin film evaporator, typically at an operating temperature of from about 130 to 300 (preferably from about 150° to about 250)° C. and at a pressure of from about 0.1 to about 30 (preferably from about 1 to about 15) mm Hg (absolute).

As noted above, it is in fact a benefit and advantage of the present invention that the process hereof results in glycoside surfactant/long chain hydrophobic alcohol solutions which are capable of being processed through thin film evaporation equipment to separate the surfactant from the alcohol without encountering unacceptable fouling or carbonizing of the heat transfer surfaces of the equipment and without forming insoluble particulate matter during the evaporation procedure.

Naturally, the glycoside surfactant products produced in accordance with the present invention can be suitably employed in any of the wide variety of household, industrial, cosmetic and agricultural applications and formulated products in which glycoside surfactants are already known to be useful and applicable. Typically, the glycoside surfactants will be manufactured and marketed as concentrated aqueous solutions containing from about 30 to about 70 (preferably from about 40 to about 60) weight percent of the glycoside surfactant on a total aqueous solution weight basis.

The present invention is further understood and illustrated by reference to the following examples in which, unless otherwise indicated, all parts and percentages are on a weight basis and all temperatures are stated in ° C.

EXAMPLE 1

A $C_{12-14}$ alkyl glucoside (having an average degree of polymerization, D.P., of approximately 1.4) solution in a $C_{12-14}$ alcohol mixture which has the composition shown in Table A below was prepared by reacting anhydrous dextrose with a $C_{12}$, $C_{13}$ and $C_{14}$ alcohol mixture at a dextrose:alcohol weight ratio of about 1:6, at a temperature of about 105° C., in the presence of about 1 mol percent (based upon dextrose) of para toluene-sulfonic acid catalyst, for a reaction period of about 8 hours and was neutralized to a pH of about 7 following the reaction using aqueous sodium hydroxide. One hundred parts by weight of the resulting reaction mixture was stirred at 735 millimeters of mercury pressure at 60° C. and 2 parts by weight of water was added to the stirred reaction mixture. The temperature of the resulting water-containing mixture was then increased to 105° C. and was held at that value for a time period of 30 minutes, during which time period a solid material formed within the reaction mixture. The solid material was then removed from the mixture by filtration and was analyzed and found to have the composition shown at column C of Table A. The filtrate was also analyzed and was found to have the composition indicated in column B of Table A.

The resulting filtrate was then stirred at a pressure of 735 mm of mercury and a temperature of 105° C. and the pressure was gradually reduced to 30 millimeters of mercury over a time period of 40 minutes and the filtrate was held at these conditions for 20 minutes to remove the water. The resulting dehydrated filtrate was found to have the composition shown in column D of Table A.

The dehydrated filtrate was then concentrated in a Leybold-Heraeus wiped film evaporator (at 205° C. and 1 mm Hg (abs)) to remove most of the unreacted $C_{12-14}$ alcohol material therefrom. As used herein abs is intended to mean absolute. The resulting concentrated $C_{12-14}$ alkyl glycoside product was found to have the composition shown in column E of Table A.

As can be seen by comparing the dry substance polydextrose + dextrose figure for column A with that of column B, the aqueous contacting operation reduced the dextrose/polydextrose content of the composition by a factor of greater than 2.5 (i.e., from 9.76% to 3.60%) on a dry substance weight basis.

TABLE A

| | A Original Neutralized Reaction Mixture as is (dry substance) | | B Filtrate as is (d.s.[1]) | | C Solid as is (d.s.) | | D Dehydrated Filtrate as is (d.s.) | | E Leybold-Heraeus Concentrate as is (d.s.) | |
|---|---|---|---|---|---|---|---|---|---|---|
| % Salts | 0.13 | (0.58) | 0.13 | (0.63) | 0.39 | (0.76) | 0.13 | (0.62) | 0.62 | (0.63) |
| % H$_2$O | 0.18 | — | 1.78 | — | 31.40 | — | 0.14 | — | 0.00 | — |
| % Total Polars (Polydextrose + Dextrose) | 2.17 | (9.76) | 0.74 | (3.60) | 33.49 | (65.31) | 0.74 | (3.53) | 1.95 | (1.97) |
| % C$_{12-14}$ DP's[2] | 6.01 | (27.02) | 5.76 | (28.00) | 14.46 | (28.20) | 5.91 | (28.21) | 29.67 | (30.03) |

TABLE A-continued

| | A<br>Original<br>Neutralized Reaction<br>Mixture as is<br>(dry substance) | | B<br>Filtrate<br>as is<br>(d.s.[1]) | | C<br>Solid<br>as is<br>(d.s.) | | D<br>Dehydrated<br>Filtrate<br>as is<br>(d.s.) | | E<br>Leybold-<br>Heraeus<br>Concentrate<br>as is (d.s.) | |
|---|---|---|---|---|---|---|---|---|---|---|
| % C12DP1[3] | 6.63 | (29.81) | 6.58 | (31.99) | 2.94 | (5.73) | 6.69 | (31.93) | 31.99 | (32.38) |
| % C13DP1[4] | 7.01 | (31.52) | 7.03 | (34.18) | 0.00 | 0.00 | 7.15 | (34.13) | 33.13 | (33.53) |
| % C13 Furanoside | 0.29 | (1.30) | 0.33 | (1.60) | 0.00 | (0.00) | 0.33 | (1.58) | 1.24 | (1.26) |
| % C14DP1[5] | 0.00 | (0.00) | 0.00 | (0.00) | 0.00 | (0.00) | 0.00 | (0.00) | 0.20 | (0.20) |
| % C12OH[6] | 37.82 | — | 37.82 | — | 8.69 | — | 38.46 | — | 0.51 | — |
| % C13OH[7] | 39.49 | — | 39.65 | — | 8.63 | — | 40.22 | — | 0.58 | — |
| % C14OH[8] | 0.27 | — | 0.19 | — | 0.00 | — | 0.23 | — | 0.20 | — |
| % Dry Substance | 22.24 | (100.0) | 20.57 | (100.0) | 51.28 | (100.0) | 20.95 | (100.0) | 99.8 | (100.0) |

[1] "d.s." means dry substance.
[2] $C_{12-14}$ DP's = $C_{12, 13\ and\ 14}$ alkyl polyglucosides
[3] $C_{12}$ DP1 = $C_{12}$ alkyl monoglucoside
[4] $C_{13}$ DP1 = $C_{13}$ alkyl monoglucoside
[5] $C_{14}$ DP1 = $C_{14}$ alkyl monoglucoside
[6] $C_{12}$ OH = $C_{12}$ fatty alcohol
[7] $C_{13}$ OH = $C_{13}$ fatty alcohol
[8] $C_{14}$ OH = $C_{14}$ fatty alcohol

EXAMPLE 2

In this example 4040 parts by weight of the long chain alkyl glycoside/long chain alcohol solution shown as the initial hydrophobic composition in Table B below was intimately admixed (i.e., vigorously shaken) at 80° C. with 1212 parts of deionized water (i.e., 30 parts water per 100 parts hydrophobic composition). A separate fluid aqueous phase formed and was separated from the hydrophobic phase at 80° C. in a DeLaval cream separator (Model GYRO TEST, at, 3450 rpm).

A clear, upper hydrophobic layer was recovered from the cream separator and was again intimately admixed (this time at 70° C.) with a second portion of deionized water (15 parts water per 100 parts hydrophobic composition) and the resulting mixture was separated in the aforementioned cream separator.

The resulting second-pass upper hydrophobic layer was recovered and was vigorously admixed at 60° C. with 15 parts by weight of deionized water per 100 parts by weight of the hydrophobic phase and the resulting aqueous and hydrophobic phases were separated from each other in the cream separator.

The resulting upper hydrophobic layer (thrice contacted with water) was analyzed and found to contain 10.4 weight percent of absorbed water and was dehydrated in a Leybold-Heraeus thin film evaporator at atmospheric pressure and 210° C.

The resulting dehydrated composition was then concentrated in the Leybold-Heraeus evaporator at 1 mm Hg and 200° C. to remove most of the long chain alcohol constituents. The approximate composition of the resulting evaporated glucoside surfactant product as measured by reverse phase liquid chromatography (RPLC) is set forth in Table B below. As can be seen from the results in the Table most of the polar materials (i.e. salts, catalyst, glucoside surfactant/unreacted long chain alcohol reaction mixture were removed during the three-step contacting process.

TABLE B

| | Initial Hydrophobic Composition (RPLC) | | Evaporated product Following Three-Step Aqueous Contacting and Deyhdration (RPLC) |
|---|---|---|---|
| | As-is Basis | d.s.* Basis | As-is Basis |
| Salts & Catalyst | .16 | 0.64 | 0.06 |
| Dextrose & Polydextrose | 1.55 | 6.20 | <.07 |
| $C_{12-15}$ polyglucosides | 8.78 | 35.11 | 32.78 |
| $C_{12}$ monoglucoside | 6.27 | 25.07 | 31.57 |
| $C_{13}$ monoglucoside | 7.38 | 29.51 | 33.78 |
| $C_{13}$ furanosides | 0.52 | 2.08 | 1.00 |
| $C_{14-15}$ monoglucosides | 0.35 | 1.40 | 0.63 |
| Dodecanol | 35.05 | | .11 |
| Tridecanol | 38.58 | | |
| Tetradecanol | 1.24 | | |
| Pentadecanol | 0.12 | | |
| Estimated Glucoside Surfactant Content (d.s.*) | | 93.2% | 99+% |
| Estimated Monoglucoside Surfactant Content (Total Glucoside Surfactant Basis | | 62.3% | 67.0% |
| Estimated Average Degree of Polymerization, DP | | 1.41 | 1.33 |

*d.s. means dry substance

While the present invention has been described and illustrated by reference to particular embodiments and examples thereof, the examples are not to be understood or intended as in any way limiting the scope of the claimed invention.

We claim:

1. A process for removing hydrophillic materials from a glycoside surfactant material which comprises: contacting the glycoside surfactant material, a hydrophobic water immiscible alcohol having from about 8 to about 30 carbon atoms, solvent for the glycoside surfactant material phase and water, the water being present in an amount at least sufficient to form a separate water containing phase and below about 50% by weight of the glycoside surfactant material and solvent, for a time sufficient to separate at least a portion of the hydrophillic material from the glycoside surfactant and separating the water containing phase from the solvent phase.

2. The process of claim 1 wherein the solvent phase comprises at least one aliphatic monohydric alcohol having from about 10 to about 24 carbon atoms.

3. A process of claim 1 wherein the solvent phase comprises, on a total composition weight basis and prior to contact with water, (a) from about 95 to about 50 weight percent of a long chain hydrophobic alcohol; (b) from about 4 to about 45 weight percent of the glycoside surfactant and (c) from about 1 to about 10 weight percent of a polysaccharide material.

4. The process of claim 1 wherein the glycoside surfactant material comprises at least one compound of the formula:

wherein R is a monovalent organic radical having from about 8 to about 30 carbon atoms; 0 is an oxygen atom; $R^1$ is a divalent hydrocarbon radical containing from 2 to about 4 carbon atoms; y is a number having an average value of from 0 to about 12; 2 is a moiety derived from a reducing saccharide containing 5 or 6 carbon atoms; and x is a number having an average value of from 1 to about 5.

5. The process of claim 4 wherein the solvent comprises at least one aliphatic alcohol containing from about 10 to about 24 carbon atoms.

6. The process of claim 4 wherein, in the formula (A), glycoside material, R is a monovalent aliphatic radical containing from about 10 to aboub 24 carbon atoms, y is zero and x has an average value of from about 1 to about 3.

7. The process of claim 1 wherein from about 1 to about 50 parts by weight of water is contacted with 100 parts by weight of the solvent phase.

8. The process of claim 1 wherein the solvent phase initially contains, on a total solvent phase weight basis, from about 0.5 to about 8 weight percent of a polysaccharide by product material prior to the contacting with water.

9. The process of claim 8 wherein the solvent phase contains, on a total solvent phase composition weight basis, less than 0.3 weight percent of the polysaccharide by product material after contacting with water.

10. The process of claim 1 wherein the process is conducted at a temperature in the range of from about 25° to about 120° C.

11. The process of claim 1 wherein the process is conducted by contacting a polysaccharide-containing solvent phase with the water for from about 0.1 to about 18 hours.

12. The process of claim 1 wherein the water immiscible solvent comprises the unreacted long chain hydrophobic alcohol and is removed from the glycoside surfactant product using a thin film evaporator operated at an elevated temperature and at subatmospheric pressure.

13. The process of claim 12 wherein the thin film evaporator is operated at a temperature in the range of from about 130° to about 300° C. and at a pressure of from about 0.1 to about 30 mm Hg (absolute).

14. The process of claim 13 wherein the long chain hydrophobic alcohol is a monohydric aliphatic alcohol containing from about 10 to about 24 carbon atoms.

15. A process for the preparation of a glycoside surfactant, which comprises:
(a) reacting a long chain hydrophobic alcohol with a saccharide reactant at an elevated temperature, in the presence of an acid catalyst, to produce a hydrophobic reaction product mixture comprising unreacted long chain hydrophobic alcohol, glucoside surfactant and polysaccharide by-product;
(b) treating the reaction product mixture by neutralizing the reaction product mixture and intimately contacting the neutralized reaction product mixture with water in an amount ranging from about 1 to about 50 parts by weight of water per 100 parts by weight of the reactive product mixture for a time period sufficient to extract at least a portion of the polysaccharide by-product out of the reaction product mixture and into said water, thereby forming a separate and distinct polysaccharide-containing aqueous phase and a purified hydrophobic reaction product phase;
(c) separating the polysaccharide-containing aqueous phase from the purified hydrophobic reaction product phase; and
(d) thereafter removing unreacted long chain hydrophobic alcohol from the purified hydrophobic reaction product phase.

16. The process of claim 15 wherein the long chain hydrophobic alcohol is a monohydric aliphatic alcohol containing from about 8 to about 30 carbon atoms.

17. The process of claim 16 wherein the saccharide reactant comprises a reducing monosaccharide containing 5 or 6 carbon atoms.

18. The process of claim 17, wherein the reaction between the saccharide reactant and the long chain hydrophobic alcohol to form the glycoside surfactant, is conducted at a temperature of from abut 80° to about 140° C. and at a pressure of from about 1 to about 100 mm Hg (absolute).

19. The process of claim 15 wherein the hydrophobic reaction product formed in step (a) comprises, on a total compostion weight basis, (a) from about 95 to about 50 weight percent of the long chain hydrophobic alcohol; (b) from about 4 to about 45 weight percent of the glycoside surfactant; and (c) from about 1 to about 10 weight percent the polysaccharide by-product.

20. The process of claim 15 wherein step (b) is conducted at a temperature of from about 25 to about 120° C.

21. The process of claim 15 wherein step (b) and the separation of step (c) are conducted in a countercurrent centrifuge.

22. The process of claim 15 wherein the hydrophobic reaction product mixture of step (a) contains, on a total composition weight basis, from about 1.5 to about 8 weight percent of the polysaccharide by-product.

23. The process of claim 22 wherein the hydrophobic reaction product mixture contains, on a total composition weight basis, less than 0.3 weight percent of the polysaccharide by-product following the contacting with water and following separation of the resulting polysaccharide-containing aqueous phase therefrom.

24. The process of claim 23 wherein, in the formula (A) glycoside surfactant, R is a monovalent organic radical containing from about 10 to about 24 carbon atoms, y is zero and x has an average value of from 1 to about 3.

25. The process of claim 15 wherein the glycoside surfactant produced corresponds to the formula:

(A)

wherein R is a monovalent organic radical containing from about 8 to about 30 carbon atoms; O is an oxygen atom; $R^1$ is a divalent hydrocarbon radical containing from 2 to about 4 carbon atoms; y is a number having an average value of from 0 to about 12; Z represents a moiety derived from a reducing saccharide containing 5 or 6 carbon atoms; and x is a number having an average value of from 1 to about 5.

26. A glycoside composition (a) which is composed predominantly of glycoside surfactant molecules of the formula:

(A)

wherein R is a hydrophobic aglycone substituent composed of a monovalent organic radical containing from about 8 to about 30 carbon atoms; 0 is an oxygen atom; $R^1$ is a divalent hydrocarbon radical containing from 2 to about 4 carbon atoms; y is a number having an average value of from 0 to about 12; Z represents a moiety derived from a reducing saccharide containing 5 to 6 carbon atoms; and x is a number having a value of from 1 to about 5; (b) which has an overall average x value of at least 1.2 and wherein, as an overall average value, the hydrophobic aglycone substituent, R, contains at least 9 carbon atoms; and (c) which contains, on a total glycoside surfactant weight basis, less than 0.5 weight percent of hydrophilic polysaccharide constituents and less than 5 weight percent of formula (A) polyglycoside species having individual x values greater than 10.

27. The composition of claim 26 wherein the hydrophobic aglycone substituent, R, contains as an overall average at least 10 carbon atoms.

28. The composition of claim 26 wherein the composition contains less than 0.25 weight percent of hydrophilic polysaccharide constituents on a total glycoside surfactant weight basis.

29. The composition of claim 26 wherein the composition contains less than 2 weight percent of formula (A) polyglycoside surfactant species having individual x values of greater than 10.

30. The composition of claim 26 wherein the glycoside surfactant as specified in item (a) of claim 26 comprises at least about 90 percent of the total weight of the composition.

* * * * *

UNITED STATES PATENT AND TRADEMARK OFFICE
CERTIFICATE OF CORRECTION

PATENT NO. : 4,987,225

DATED : January 22, 1991

INVENTOR(S) : Carl Pickens et al.

It is certified that error appears in the above-identified patent and that said Letters Patent is hereby corrected as shown below:

Column 12 - 13:

Cancel Claim 1 as written and insert the following:

--A process for removing hydrophilic materials from a glycoside surfactant material which comprises: contacting a solvent phase comprising the glycoside surfactant material and a hydrophobic water immiscible alcohol solvent for the glycoside surfactant material, having from about 8 to about 30 carbon atoms with water, the water being present in an amount at least sufficient to form a separate water containing phase and below about 50% by weight of the solvent phase, for a time sufficient to separate at least a portion of the hydrophilic material from the glycoside surfactant and separating the water containing phase from the solvent phase.--

Signed and Sealed this

Twenty-first Day of July, 1992

*Attest:*

DOUGLAS B. COMER

*Attesting Officer*  *Acting Commissioner of Patents and Trademarks*